US012721696B2

(12) United States Patent
Smart

(10) Patent No.: US 12,721,696 B2
(45) Date of Patent: Sep. 1, 2026

(54) DRYNESS TESTING DEVICE

(71) Applicant: SMARTLINE HOLDINGS PTY LTD, Queensland (AU)

(72) Inventor: William Hugh Dawkins Smart, Queensland (AU)

(73) Assignee: SMARTLINE HOLDINGS PTY LTD, Queensland (AU)

( * ) Notice: Subject to any disclaimer, the term of this patent is extended or adjusted under 35 U.S.C. 154(b) by 907 days.

(21) Appl. No.: 17/912,724

(22) PCT Filed: Mar. 18, 2021

(86) PCT No.: PCT/AU2021/050247
§ 371 (c)(1),
(2) Date: Sep. 19, 2022

(87) PCT Pub. No.: WO2021/184074
PCT Pub. Date: Sep. 23, 2021

(65) Prior Publication Data

US 2023/0144987 A1 May 11, 2023

(30) Foreign Application Priority Data

Mar. 20, 2020 (AU) ................................ 2020900867

(51) Int. Cl.
*A61B 90/70* (2016.01)

(52) U.S. Cl.
CPC ........ *A61B 90/70* (2016.02); *A61B 2090/701* (2016.02); *A61B 2090/702* (2016.02); *A61L 2202/14* (2013.01)

(58) Field of Classification Search
CPC ........... A61L 2202/14; A61L 2202/122; A61L 2202/24; C12Q 1/22; A61C 19/002
USPC ......... 73/861.42, 24.04, 25.04, 29.01, 23.24, 73/23.25, 73, 335.06
See application file for complete search history.

(56) References Cited

U.S. PATENT DOCUMENTS 5,317,896 A * 6/1994 Sheth ........................ A61L 2/24 436/39
5,824,918 A * 10/1998 Zuk ...................... G01N 17/002 73/147
8,757,737 B2 6/2014 Smart
11,273,230 B1 * 3/2022 Baumgartner ............ A61L 2/26
(Continued)

FOREIGN PATENT DOCUMENTS

EP 1502538 A1 * 2/2005 ............... A61L 2/26
EP 3459432 A1 3/2019
(Continued)

OTHER PUBLICATIONS

International Search Report and Written Opinion for International Application No. PCT/AU2021/050247 Dated Jun. 30, 2021, 12 pages long.

(Continued)

*Primary Examiner* — John E Breene
*Assistant Examiner* — Truong D Phan
(74) *Attorney, Agent, or Firm* — Wegman Hessler

(57) ABSTRACT

The present invention is directed to a device for testing the dryness of a cleaned medical instrument such as an endoscope. The preferred embodiment tests the air drawn through the medical instrument by measuring the differential pressure, humidity and temperature of the air.

18 Claims, 9 Drawing Sheets

(56) References Cited

U.S. PATENT DOCUMENTS

2006/0252991 A1* 11/2006 Kubach .................. G01M 3/26 600/118
2007/0154346 A1* 7/2007 Lin ........................ A61L 2/186 422/28
2012/0111325 A1* 5/2012 Hrkach ............. A61M 15/0028 128/203.15
2012/0139398 A1* 6/2012 Smart .................... A61B 50/10 137/1
2013/0096375 A1* 4/2013 Iyama ................ A61B 1/00096 600/103
2015/0272571 A1* 10/2015 Leimbach ................. A61L 2/16 227/175.1
2017/0274108 A1* 9/2017 Vinteler .................... A61L 2/14
2017/0303822 A1* 10/2017 Allsworth .......... B01D 46/0028
2018/0177563 A1 6/2018 Smart
2019/0015777 A1* 1/2019 Urwin .................. B01D 53/261

FOREIGN PATENT DOCUMENTS

GB 2568304 A * 5/2019 ............... A61L 2/26
WO 9800176 A1 1/1998
WO 20180024690 A1 2/2018

OTHER PUBLICATIONS

Written Opinion for International Application No. PCT/AU2021/050247 Dated Jan. 28, 2022 5 pages long.
International Preliminary Report on Patentability for International Application No. PCT/AU2021/050247 Dated Jul. 6, 2022, 17 pages long.
Extended European Search Report of Corresponding International Application No. PCT/AU2021/050247 dated Mar. 14, 2024, 10 pages.

* cited by examiner

DRYNESS TESTING DEVICE

CROSS REFERENCE TO RELATED APPLICATION

This application is a national phase of International Patent Application No. PCT/AU2021/050247 filed Mar. 18, 2021, which claims the priority filing benefit of Australian Patent Application No. 2020900867 filed Mar. 20, 2020, which are incorporated herein by reference in their entirety.

FIELD OF INVENTION

The present invention relates to a device for testing the dryness of a cleaned medical instrument. In particular, the present invention relates, but is not limited, to a device for testing the dryness of an endoscope. Reference in the present specification to an endoscope is by way of example and the invention is not limited to use with an endoscope.

BACKGROUND OF THE INVENTION

An endoscope is a medical instrument that is used to examine an internal cavity of a patient, in particular the gastrointestinal tract. After use, the endoscope is washed and cleaned so it can be reused. The endoscope is an expensive instrument, and has sensitive sensors and cameras. Cleaning the endoscope consequently needs to be relatively gentle and it cannot be subject to high temperature autoclaving.

After washing, an endoscope is dried in a specific drying cabinet with a controlled environment to place the endoscope in a high level disinfected state after cleaning. Generally, an endoscope is left in the drying cabinet for a set period of time that is deemed to dry and sterilize the endoscope.

The test for dryness for endoscope has been standardized in Europe, documented as EN 16442:2015 *Controlled environment storage cabinet for processed thermolabile endoscopes*. The method of testing dryness involves the use of copper (II) sulphate test paper or cobalt chloride test paper, and compressed air. Generally, at the end of the drying phase, the endoscope is removed from the cabinet. The distal end of the endoscope is directed towards a horizontal piece of anhydrous copper (II) sulphate paper at a distance of 50 mm to 100 mm. Medical grade air at a positive pressure up to 120 kPA (or 15 psi) is flushed through each channel system. The test paper will change colour from blue to pink if water was expelled from the endoscope. The user then assumes the dryness level of the interior of the endoscope after reprocessing. A problem with testing dryness is that, to test the endoscope, it requires removing the endoscope from the drying and storing cabinet and consequently the scope will not be at a high level of disinfection state.

Incomplete drying results in residual moisture remaining within an internal channel of the endoscope. Residual moisture within the internal channel allows microorganisms to survive and grow to form biofilms. Using a reusable endoscope that has microorganisms in the internal channels of the endoscope can lead to possible infection in the next patient.

Currently there is no device or method that quantitively tests for dryness of an endoscope and disinfection after they have been cleaned.

OBJECT OF THE INVENTION

It is an object of the present invention to provide a testing device, a system and a method of use which overcomes or ameliorates one or more of the disadvantages described above, or which at least provides a useful alternative.

SUMMARY OF THE INVENTION

The inventors recognized the need to quantitatively test the dryness level of the individual internal channels of a reusable endoscope after reprocessing. Specifically, the inventors found that the dryness level of the internal channel of the endoscope are interrelated to the number of microorganisms. The inventors consider the problem of dryness with respect to the internal channel of the endoscopes in order to have a way of measuring the level of dryness within a reprocessed endoscope. Furthermore they recognised the need to test each individual internal channel and avoid the blowing or pushing of air through the device as this would result in an amalgamation of air coming out of the distal tip of the scope.

The inventors also recognized the benefits of keeping the reprocessed endoscope in the high level disinfected condition (or substantially sterile) during the dryness testing. The high level disinfected condition is considered as no contamination due to further handling of the instruments after reprocessing and prior to the next use.

Through extensive trial and experimentation on various solutions, the inventors have settled on the current invention in order to help minimizing the level of microbiological activity within a reprocessed endoscope, thereby lower the risk of patient-to-patient infection.

In one aspect the present invention broadly resides in a dryness testing device for a medical instrument, the device including:

- one or more chambers configured to be connectable to the medical instrument and receive air flow from the medical instrument; and
- one or more sensors configured to assist in determining one or more flow rates, humidity and or temperature of air being drawn through the medical instrument and drawn through the one or more chambers; wherein the measurements from the one or more sensors provides an indication of the dryness of the medical instrument.

The indication of the dryness of the medical instrument is preferably determined from the processed sensor measurements to provide quantitative values and or qualitative comparisons with external air. Preferably the qualitative comparisons use immediate external air where air is drawn from external of the medical instrument.

Each of the one or more chambers preferably has an internal dividing wall that forms a first compartment and a second compartment. The internal dividing wall preferably has a substantially centred opening to allow air to pass through the first compartment to the second compartment.

The one or more chambers preferably includes an inlet and an outlet. The inlet is preferably configured to include a releasable coupling for connecting to the medical instrument. The outlet is preferably configured to include a releasable coupling for connecting to an extraction means. The inlet and outlet are preferably located at opposite ends of the chamber.

The inlet preferably further includes a filter. Preferably, the filter includes a mesh made from nylon, polyester, polyethylene, polypropylene, polyurethane, viscose, glass fibre, steel filaments or a combination thereof.

In a first preferred embodiment, the filter is adapted to filter out particles from air passing through the inlet into the one or more chambers. Particles present in the air passing through the inlet into the one or more chambers can cause blockage at the inlet and or at the substantially centred opening of the internal dividing wall. The blockage can prevent or reduce the flow of air passing through to the first chamber and then to the second chamber.

Preferably, the filter is adapted to filter out particles that can block or pass through an inlet diameter of 0.6 mm. Preferably the filter is of suitable material and pore size to prevent particles from blocking the inlet and or the substantially centred opening.

In a second preferred embodiment, the filter is adapted to breakup droplets of liquid that pass through the filter into a plurality of small droplets of liquid. The plurality of small droplets of liquid preferably has a size that is smaller than the droplets of liquid that enter the filter. Preferably, the filter is adapted to trap the plurality of small droplets of liquid to promote evaporation.

Droplets of liquid from the medical instrument may enter and remain in the dryness testing device. The presence of the droplets of liquid in the dryness testing device can affect the accuracy of the one or more sensors in determining the humidity of air being drawn through the medical instrument and drawn through the one or more chambers. The filter preferably breaks up the droplets of liquid into a plurality of small droplets of liquid and increases the surface area of the droplets of liquid to promote evaporation.

Preferably, during use the air is drawn through one or more internal channels of the medical instrument and then to the one or more chambers. Preferably, one internal channel is connected to one chamber.

Each of the one or more chambers preferably has one or more sensors.

One of the one or more sensors is preferably a pressure sensor.

In a preferred embodiment, the pressure sensor is a differential pressure sensor that measures the pressure of the air in the first compartment and the pressure of the air in the second compartment of the chamber. From the two pressure readings, the pressure difference is recorded and is used to calculate the air flow rate between the two compartments.

One of the one or more sensors is preferably a humidity and temperature sensor. The humidity and temperature sensor preferably measures the humidity and temperature of the air in the chamber.

In a preferred embodiment, the humidity and temperature sensor measures the air in the second compartment of the chamber.

In a preferred embodiment, each of the one or more chambers has at least one pressure sensor and at least one humidity and temperature sensor.

Preferably, the one or more sensors sends data to a processor that collects and processes the data from the one or more sensors.

In a first preferred embodiment, the processor is configured to determine an absolute humidity value for each chamber. The absolute humidity value is determined from the air flow rate, the humidity and the temperature data. The absolute humidity value is the mass of moisture present in a given volume of air.

In a second preferred embodiment, the processor is preferably configured to compare the air flow rate associated with the medical instrument and a predetermined range of air flow rates, and provide an indication of a problem associated with the drying of the medical instrument. Problems associated with the drying of the medical instrument can include that the medical instrument is not connected, partially connected or incorrectly connected to the dryness testing device, and or that there is a blockage within the internal channel of the medical instrument, within the connection between the medical instrument and the dryness testing device and or within the dryness testing device. Preferably, when the processor determined that the air flow rate associated with the medical instrument is below or above a predetermined range of air flow rates, the processor sends a signal to an alarm system to indicate that there is a problem associated with the drying of the medical instrument.

Preferably, if the air flow rate associated with the medical instrument is above a predetermined range of air flow rates, it is indicative that the medical instrument is not connected, partially connected or incorrectly connected to the dryness testing device. Preferably, if the air flow rate associated with the medical instrument is below a predetermined range of air flow rates, it is indicative that there is a blockage within the internal channel of the medical instrument, within the connection between the medical instrument and the dryness testing device and or within the dryness testing device.

The predetermined range of air flow rates is preferably in a range of substantially two to three liters per minute (L/min).

Preferably, the medical instrument is a reusable medical instrument. More preferably, the medical instrument is in the form of a scope. Most preferably, the medical instrument is an endoscope, gastroscope, bronchoscope, duodenoscope, enterscope, ultrasound scope, toe probe, truss probe, Brachy probe and/or ENT flexible or rigid scope.

The medical instrument preferably includes one or more ports to be respectively connected to the one or more chambers.

Preferably, the dryness testing device includes an additional chamber configured to draw air external to the medical instrument, and measures the external air in order to compare with the quality of the air being drawn through the medical instrument. When the quality of the air being drawn through the medical instrument is substantially the same as the quality of the air that is external to the medical instrument, the medical instrument can be considered as dried.

The dryness testing device can be used as a separate independent device or be incorporated within a drying and storing cabinet for the medical instrument.

In a first preferred embodiment, the dryness testing device is incorporated within a drying and storing cabinet and configured to be used as an in-cabinet dryness testing system. In this embodiment, the dryness testing device preferably draws air from the drying and storing cabinet into the additional chamber. The air drawn from the drying and storing cabinet into the additional chamber is preferably used as the external air for comparing with the quality of the air being drawn through the medical instrument.

In a second preferred embodiment, the dryness testing device is a separate independent device and configured to be used out of the drying and storing cabinet but in communication with the air flow drawn through the medical instrument. In this embodiment, the dryness testing device preferably draws air from a testing environment outside of the drying and storing cabinet into the additional chamber. The air drawn from the testing environment outside of the drying and storing cabinet is preferably used as the external air for comparing with the quality of the air being drawn through the medical instrument.

To test whether the dried endoscope is also substantially sterile and at a high level of disinfection, a further test is conducted and the results extrapolated to similarly dried endoscopes.

According to the guidance from the Department of Health and Social Care of the United Kingdom ("*Health Technical Memorandum* 01-06*: Decontamination of flexible endoscopes. Part E: Testing methods*", last updated 30 Jun. 2016), if a 100 ml of water was passaged through the dried endoscope, and the passaged water was plated, then a measurement of 10 or less colony-forming unit (cfu) from the passaged water would classify the dried endoscope as being substantially sterile (or at a high level of disinfection). The applicant notes that this test is only one example of a sterility test, and other tests and qualifications can be applied.

While it is not necessary to test every dried endoscope for disinfection (or substantial sterility), a sample of a dried endoscope from a batch of dried endoscopes can be tested, and a determination of sterility from the sample can be applied and extended to the entire batch of dried endoscopes.

In another aspect the present invention is a dryness testing system, the system including:

one or more dryness testing devices as described above; and one or more extraction means as described above.

The extraction means preferably is an extraction pump or an extraction fan.

The system preferably further includes one or more HEPA filters connected to the outlet of the dryness testing device.

The system preferably further includes a processor that receives data generated from the one or more sensors. The processor preferably includes a multiplexer and an interface board data processing unit. Preferably, a USB drive can be used to retrieve data from the processor and display the data on a computer. Data can also be sent via a wired or wireless connection from the processor to a computer.

The system preferably further includes an alarm system that receives a signal from the processor as herein described to indicate that there is a problem associated with the drying of the medical instrument. The alarm system preferably includes means to notify an operator whether the one or more ports of the medical instrument are successfully connected to the one or more chambers of the dryness testing device, and whether there is no blockage within the internal channel of the medical instrument, within the connection between the medical instrument and the dryness testing device, and within the dryness testing device.

The system is preferably configured to be used with a drying and storing cabinet for the medical instrument.

In a first preferred embodiment, the system is configured as an in-cabinet dryness testing system. In this embodiment, the dryness testing device is preferably configured to draw air from the drying and storing cabinet into the additional chamber. The drying and storing cabinet preferably includes a manifold that is configured to connect the HEPA filter to the cabinet, to allow air that pass through the HEPA filter to return into the cabinet.

In a second preferred embodiment, the system is configured as an out-of-cabinet dryness testing system. In this embodiment, the dryness testing device is preferably configured to draw air from a testing environment outside of the drying and storing cabinet into the additional chamber. The air that passes though the HEPA filter is preferably release to the environment outside of the drying and storing cabinet.

The cabinet can optionally be a blow-drying type drying and storing cabinet where air is pumped through the medical instrument. In this embodiment, the system preferably further includes a switch that allows air to bypass the dryness testing device to pump through the internal channel of the medical instrument.

Preferably, the switch can control the air flow to bypass the dryness testing device or to draw air through the medical instrument into the dryness testing device.

In another aspect, the present invention is a method for dryness testing, the method including the steps of:

connecting a medical instrument to the one or more chambers of the dryness testing device as described above;

determining one or more flow rates, humidity and or temperature of air being drawn through the medical instrument and drawn through the one or more chambers; and determining a dryness condition of the medical instrument from the one or more flow rate, humidity and/or temperature.

Preferably, the step of connecting the medical instrument to the one or more chambers of the dryness testing device includes connecting one or more ports of the medical instrument to the inlet of the one or more chambers.

Preferably, the step of determining the one or more flow rates, humidity and/or temperature of air being drawn through the medical instrument and drawn through the one or more chambers includes measuring the air flow rate, the humidity, and or temperature of the air in the one or more chambers.

Preferably, the step of measuring the air flow rate includes measuring the pressure of the air in the first compartment and the pressure of the air in the second compartment of the chamber. From the two pressure readings, the pressure difference is recorded and use to calculate the air flow rate between the two compartments.

Preferably, the step of determining the dryness condition of the medical instrument includes determining the absolute humidity value based on the air flow rate, humidity and or temperature.

Optionally, the method may include a disinfection value based on the results of testing a dried medical instrument for a microorganism count and extrapolate the findings to other similarly dried medical instruments.

Prior to the step of determining the dryness condition of the medical instrument, the method of dryness testing preferably further includes a step of determining the connection between the medical instrument to the one or more chambers of the dryness testing device.

Preferably, the step of determining the connection includes the steps of:

comparing the air flow rate associated with the medical instrument and a predetermined range of air flow rates; and providing an indication of a problem associated with the drying of the medical instrument when the air flow rate associated with the medical instrument is above or below the predetermined range of air flow rates.

Preferably, the predetermined range of air flow rates is in the range of substantially two to three liters per minute (L/min).

Preferably, the problem is selected from one or more of the following: that the medical instrument is not connected, partially connected or incorrectly connected to the dryness testing device, and or that there is a blockage within the internal channel of the medical instrument and or the connection between the medical instrument and the dryness testing device.

Preferably, the step of providing an indication of a problem associated with the medical instrument includes the step of sending a signal to the alarm system to indicate that there is a problem associated with the drying of the medical instrument.

The features described with respect to one aspect also apply where applicable to all other aspects of the invention. Furthermore, different combinations of described features are herein described and claimed even when not expressly stated.

BRIEF DESCRIPTION OF THE DRAWINGS

In order that the present invention can be more readily understood, reference will now be made to the accompanying drawings which illustrate preferred embodiments of the invention and wherein.

DETAILED DESCRIPTION OF THE PREFERRED EMBODIMENTS

Figure 1:
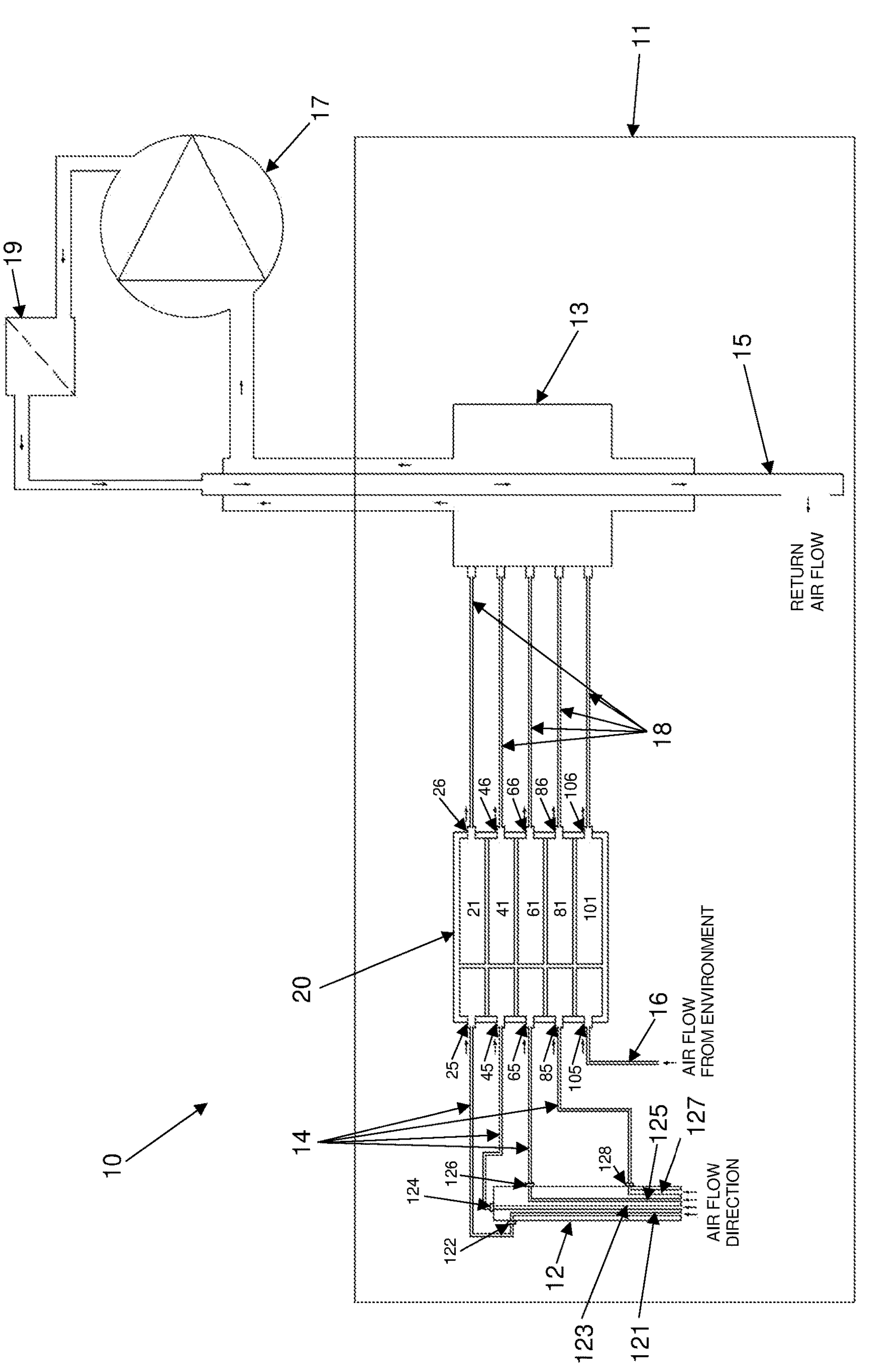
FIG. 1 is a diagram of a dryness testing device and an in-cabinet dryness testing system of a first preferred embodiment.
Figure 2:
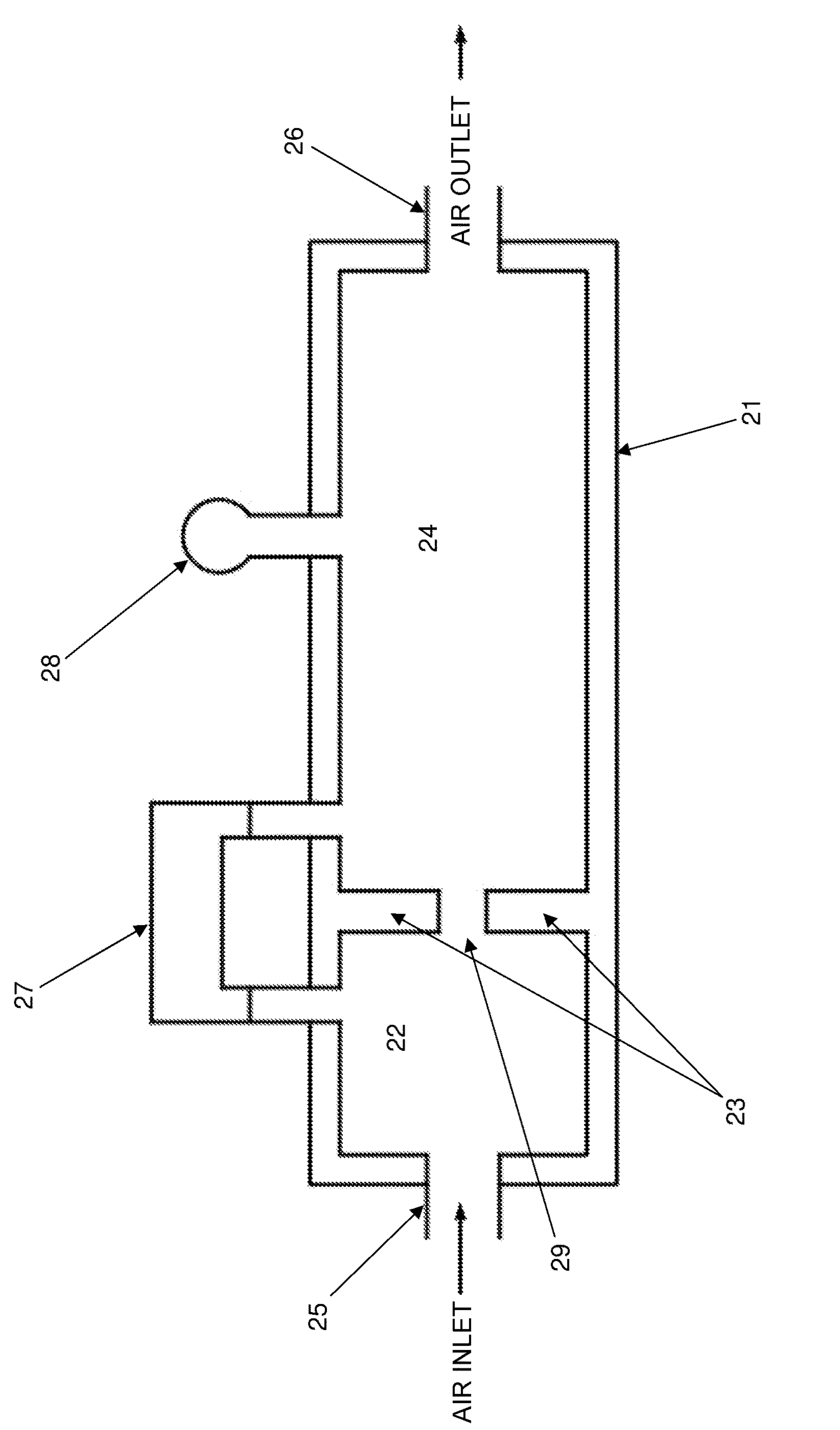
FIG. 2 is a diagram of a chamber of the dryness testing device as shown in FIG. 1.

With reference to FIGS. 1 and 2, there is shown the in-cabinet dryness testing system 10 according to a first preferred embodiment. The in-cabinet dryness testing system 10 includes a cabinet 11; a medical instrument in the form of an endoscope 12; a dryness testing device 20; a cabinet manifold 13, an extraction pump 17 and a HEPA filter 19. The extraction pump 17 causes air to be drawn through the system and the endoscope 12, then through the dryness testing device 20 and then into the cabinet manifold 13.

The dryness testing device 20 includes five chambers 21, 41, 61, 81, 101 with five air inlets 25, 45, 65, 85, 105 and five air outlets 26, 46, 66, 86, 106 respectively.

Each of the five chambers 21, 41, 61, 81, and 101 has the same configuration. With particular reference to FIG. 2, there is shown the chamber 21 in more details as an example for chambers 41, 61, 81, and 101. The chamber 21 includes a first compartment 22 and a second compartment 24 that is separated by an internal dividing wall 23, an air inlet 25, an air outlet 26, a differential pressure sensor 27 and a humidity and temperature sensor 28. The internal dividing wall 23 has an opening 29 that is substantially at the centre of the wall 23.

The differential pressure sensor 27 is configured to measure the air in the first compartment 22 and second compartment 24. The humidity and pressure sensor 28 is configured to measure the air in the second compartment 24.

When in use, air enters the chamber 21 through the air inlet 25 and is drawn into the first compartment 22, where the differential pressure sensor 27 can measure the pressure of the air in the first compartment 22. The air is then drawn from the first compartment 22 through the opening 29 of internal dividing wall 23 into the second compartment 24. The differential pressure sensor 27 can then measure the pressure of the air in the second compartment 24. The humidity and the temperature of the air are also measured in the second compartment 24 by the humidity and temperature sensor 28. The air will then be drawn from the chamber 21 through the air outlet 26.

The air inlet 25 further includes a filter to filter out particles from air that is drawn through the dryness testing device 20 (not shown in the figure). Particles present in the air that enter the dryness testing device 20 can lead to a blockage at the air inlet 25 and or at the opening 29 that prevents air flowing through the first compartment 22 and the second compartment 24. The accuracy of the sensors and the measurements of the air pressure in the first compartment 22 and second compartment 24 can be affected by the blockage. The filter at the air inlet 25 helps to prevent blockage of the air inlet 25 and or at the opening 29 by the particles.

The filter at the air inlet 25 can also breakup water droplets present in the air that is drawn from the endoscope 12 to the dryness testing device 20. Water droplets from the endoscope 12 may enter and remain in the dryness testing device 20. The presence of the water droplets in the dryness testing device 20 can affect the accuracy of the humidity and temperature sensor 28. Breaking up the water droplets into a plurality of small water droplets by the filter increases the surface area of the water droplets to promote evaporation. The presence of the filter to promote the evaporation of the water droplets helps to reduce the error margin in determining the humidity of the air being drawn through the endoscope 12 and drawn through the second compartment 24.

With reference to FIG. 1, the endoscope 12 includes internal channels 121, 123, 125, and 127 and ports 122, 124, 126, and 128 respectively on the exterior of the endoscope. In other embodiments where there are scopes with five or more internal channels, they can be monitored in a similar way using larger testing device.

The four air inlets 25, 45, 65, and 85 of the dryness testing device 20 are configured to be respectively connected to the ports 122, 124, 126, and 128 on the endoscope 12 via separate silicone tubes 14. The air is then drawn from the internal channels 121, 123, 125, and 127 of the endoscope 12 into the four separate chambers 21, 41, 61, 81 of the dryness testing device 20. The fifth air inlet 105 of the dryness testing device 20 is configured to draw air in the cabinet 11. That is, air is drawn from an external source via a separate silicone tube 16. The air drawn from the external source is termed cabinet air. The cabinet air is drawn into a separate chamber 101 of the dryness testing device 20. The pressure difference, the humidity and the temperature of the air that is drawn through the five separate chambers 21, 41, 61, 81, and 101 of the dryness testing device 20 are measured. It should be noted that the air drawn into each of chambers 21, 41, 61, 81, and 101 that came from different sources (that is, air from each of the internal channels 121, 123, 125, 127 and air in the cabinet) are not mixed.

The air outlets 26, 46, 66, 86, and 106 of the dryness testing device 20 are configured to be connected to the cabinet manifold 13 via silicone tubes 18. The cabinet manifold 13 thus collects the air that is drawn from the dryness testing device 20. The cabinet manifold 13 is also connected to the extraction pump 17. The collected air in the cabinet manifold 13 is then pumped through the HEPA filter 19. The filtered air then enters a cabinet pipe 15 that is part of the cabinet manifold 13, and return into the cabinet 11. It should be noted that the air in the cabinet manifold 13 and the air in the cabinet pipe 15 are not mixed.

Figure 3:
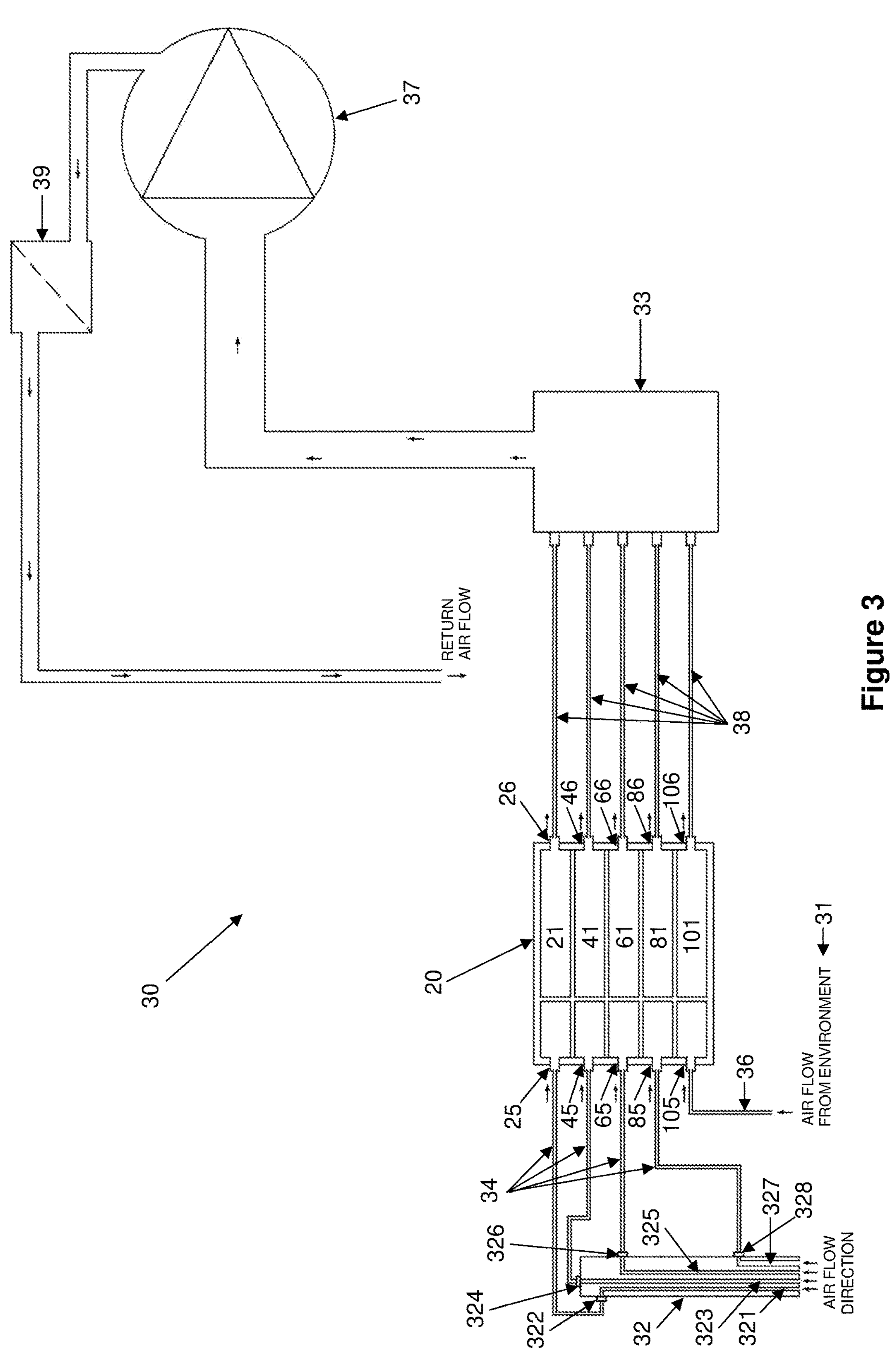
FIG. 3 is a diagram of a dryness testing device and an out-of-cabinet dryness testing system of a second preferred embodiment.

With reference to FIG. 3, there is shown the out-of-cabinet dryness testing system 30 according to a second preferred embodiment. The out-of-cabinet dryness testing system 30 is similar to the in-cabinet dryness testing system 10 as shown in FIG. 1. However, the out-of-cabinet dryness testing system 30 does not include a cabinet and the air is not recirculated.

The dryness testing device 20 as shown in FIG. 1 can also be used in the out-of-cabinet dryness testing system 30. In this configuration, the four air inlets 25, 45, 65, and 85 of the dryness testing device 20 are configured to be respectively connected to the ports 322, 324, 326, and 328 on the endoscope 32 via separate silicone tubes 34. The air is drawn from the internal channels 321, 323, 325, and 327 of the endoscope 32 into the four separate chambers 21, 41, 61, and 81 of the dryness testing device 20. The fifth air inlet 105 of the dryness testing device 20 is configured to draw air from the testing environment 31. That is, air is drawn from an external source via a separate silicone tube 36. The air drawn from the external source is termed testing environment air. The testing environment air is drawn into the separate chamber 101 of the dryness testing device 20. The pressure difference, the humidity and the temperature of the air that is drawn from the endoscope 32 and from the testing environment 31 can be measured by the dryness testing device 20.

The air drawn out of the dryness testing device 20 is collected in a manifold 33 via silicone tubes 38. The manifold 33 is also connected to the extraction pump 37. The extraction pump 37 causes air to be drawn through the out-of-cabinet dryness testing system 30 and the endoscope 32, then through the dryness testing device 20 and then into the manifold 33. The collected air in the manifold 33 is then pumped through the HEPA filter 39. The filtered air then returns to the testing environment 31.

Figure 4:
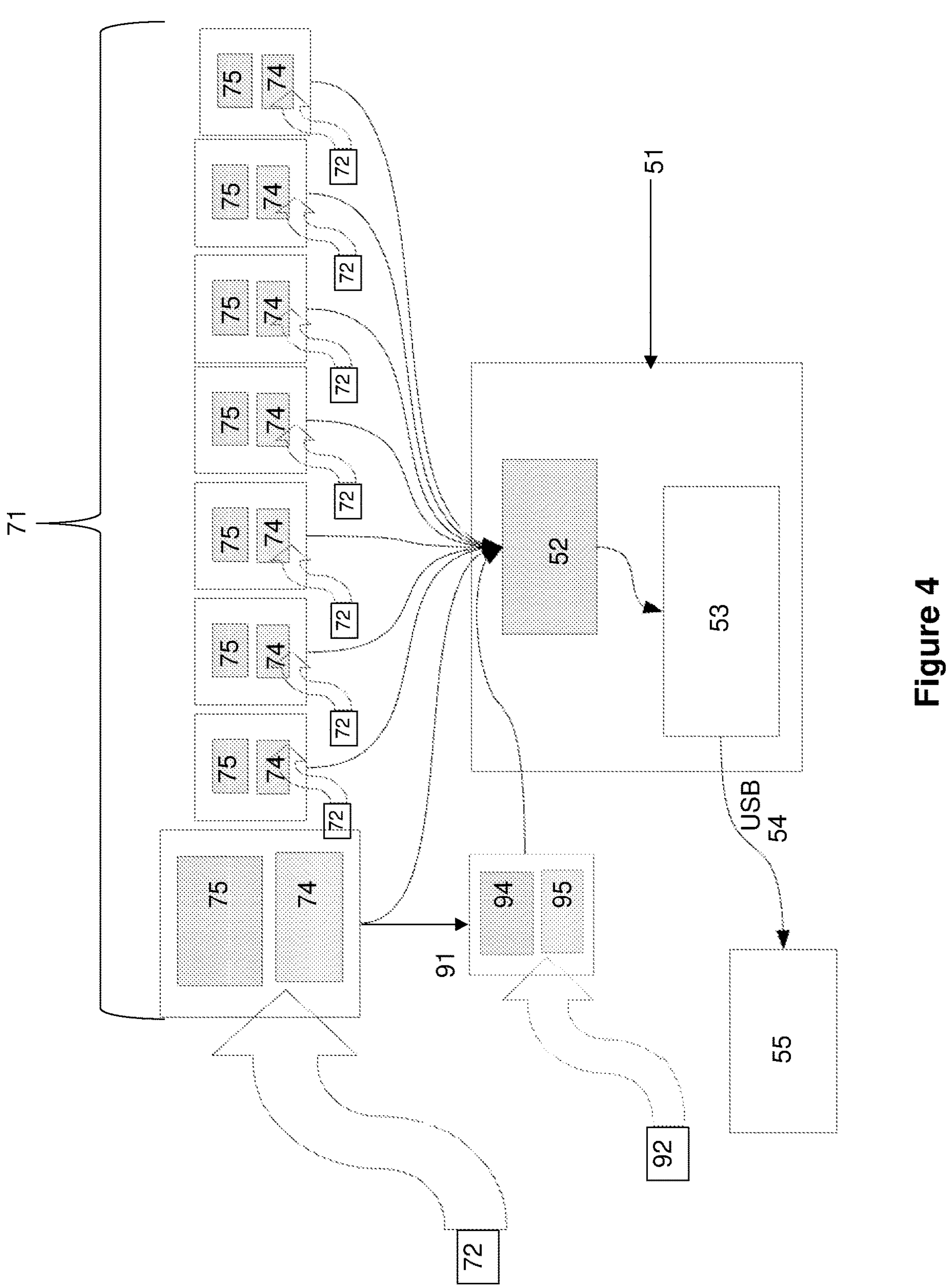
FIG. 4 is a diagram that shows the communication connection between the various components of the system of the first and second preferred embodiments.

With reference to FIG. 4, there is shown the communication connection between the various components of the system of the first and second preferred embodiment. There is a processor 51 that includes a multiplexer 52 and an interface board data processing unit 53. The processor 51 is configured to communicate with multiple chambers 71. The multiple chambers 71 are configured to draw air from multiple internal endoscope channels 72.

The processor is also configured to communicate with one chamber 91. The chamber 91 is configured to draw air from the testing environment 92 (in-cabinet or out-of-cabinet).

The processor 51 is configured to collect and process the air flow rate data 74 and the humidity and temperature data 75 from multiple chambers 71. The processor 51 is also configured to collect and process the air flow rate data 94 and the humidity and temperature data 95 from chamber 91.

The processed data from the processor 51 can be retrieved by a USB drive 54 and displayed on a computer 55 for a user.

The processor 51 is also configured to compare the air flow rate data 74 and a predetermined range of air flow rates, and provide an indication of a problem associated with the drying of the internal endoscope channel 72. When the processor 51 determines that the air flow rate data 74 is above a predetermined range of air flow rates of two to three L/min, the processor 51 sends a signal to an alarm system (not shown in the figure) to indicate that the internal endoscope channel 72 is not connected, partially connected or incorrectly connected to the chamber 71. When the processor 51 determines that the air flow rate data 74 is below a predetermined range of air flow rates of two to three L/min, the processor 51 sends a signal to the alarm system to indicate that there is a blockage within the internal endoscope channel 72 and/or the connection between the chamber 71 and the internal endoscope channel 72.

Figure 5:
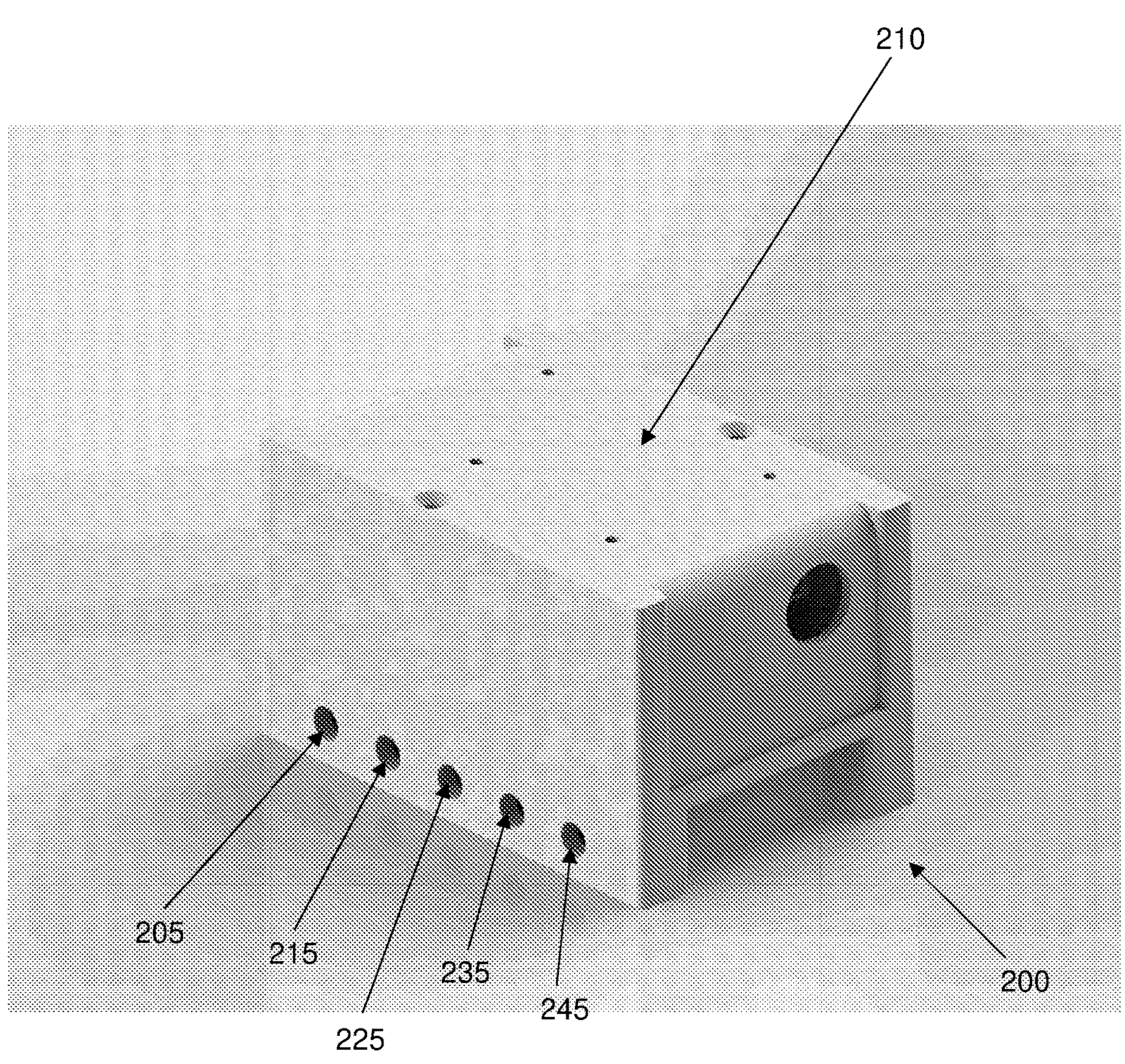
FIG. 5 is a three-dimension (3D) diagram that shows the entire dryness testing device with five air inlets/outlets and an outer casing cover.

With reference to FIG. 5, there is shown the 3D model of a dryness testing device 200 with five air inlets 205, 215, 225, 235, and 245 and an outer casing cover 210. The dryness testing device may be formed from a variety of plastics known in the art.

Figure 6:
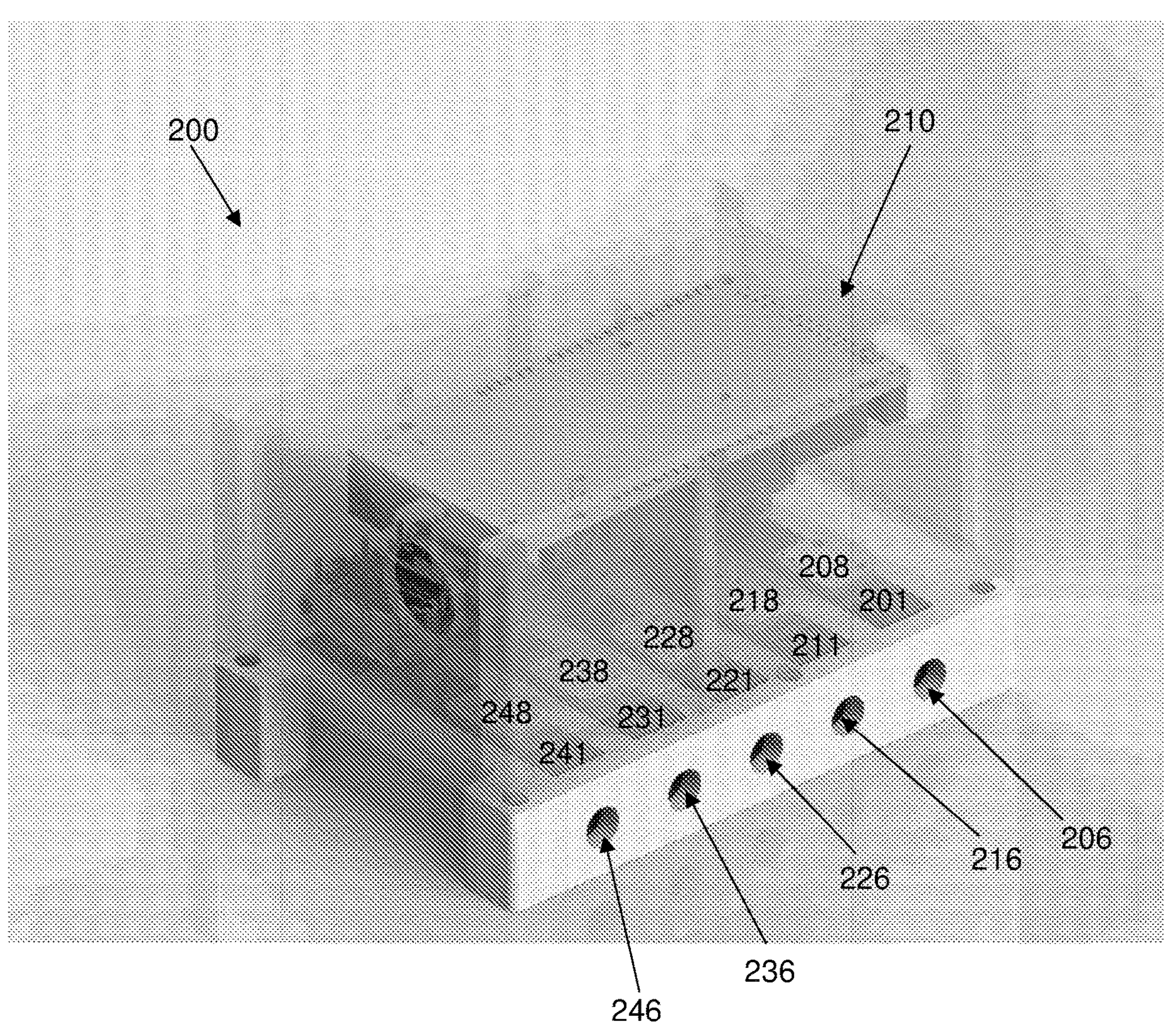
FIG. 6 is a 3D diagram of the dryness testing device of FIG. 5, where the outer casing cover is transparent.

With reference to FIG. 6, there is shown the 3D model of the dryness testing device 200 of FIG. 5, where the outer casing cover 210 is transparent. The dryness testing device 200 includes five chambers 201, 211, 221, 231, and 241 with five air outlets 206, 216, 226, 236, and 246 and five humidity and temperature sensors 208, 218, 228, 238, and 248.

Figure 7:
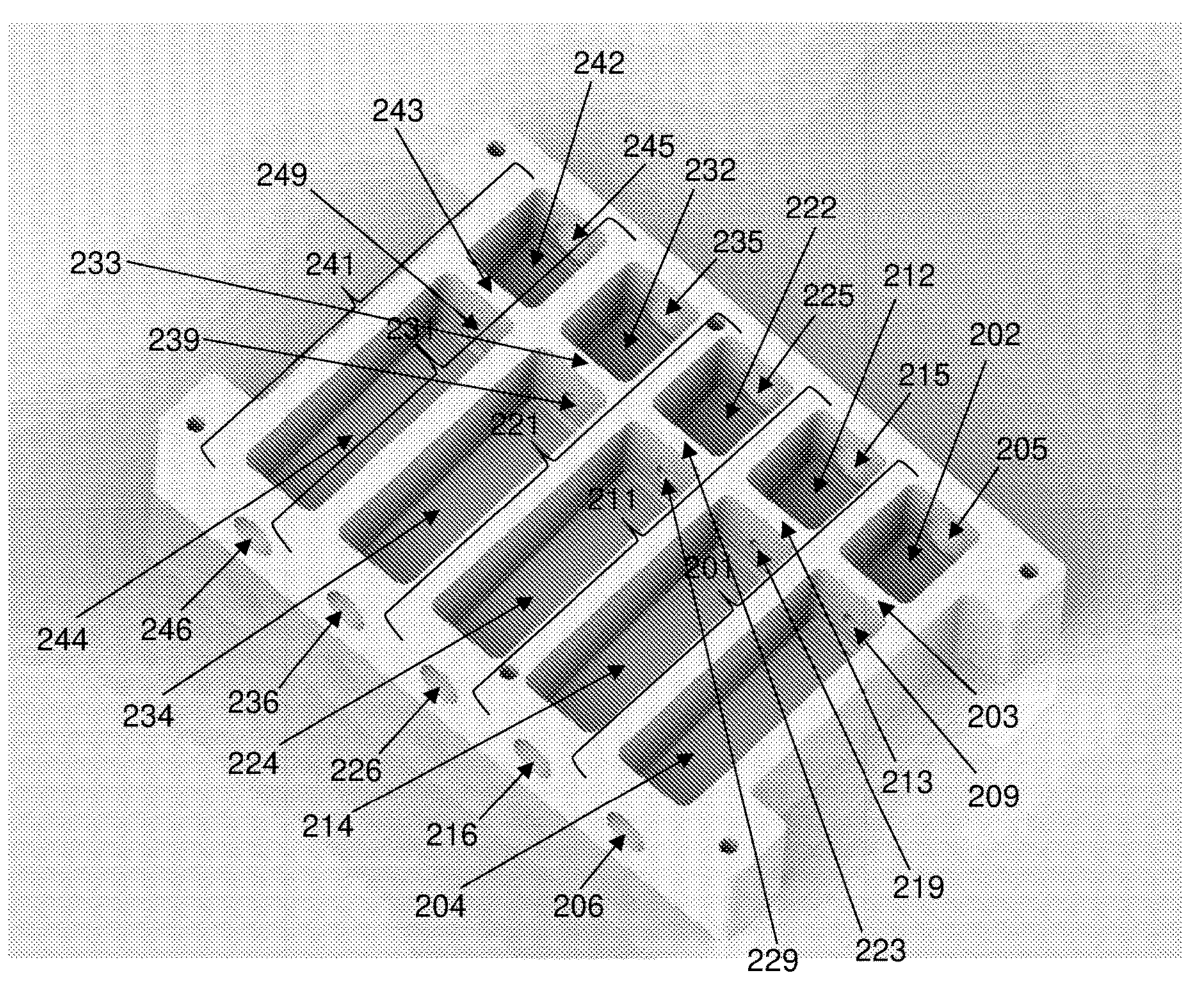
FIG. 7 is a 3D diagram of the chambers of the dryness testing device of FIGS. 5 and 6.

With reference to FIG. 7, there is shown the 3D model of the configuration of the five chambers 201, 211, 221, 231, and 241 of the dryness testing device 200 of FIGS. 5 and 6. Each chambers include first compartments 202, 212, 222, 232, and 242 and second compartments 204, 214, 224, 234 and 244. The first compartments and second compartments are separated by internal dividing walls 203, 213, 223, 233, and 243. The internal dividing walls each has an opening 209, 219, 229, 239, and 249 to allow air drawn from the first compartment into the second compartment. Each chamber also includes air inlets 205, 215, 225, 235, and 245 to receive the air drawn from an endoscope, and air outlets 206, 216, 226, 236, and 246 to draw air out of the chambers.

Figure 8:
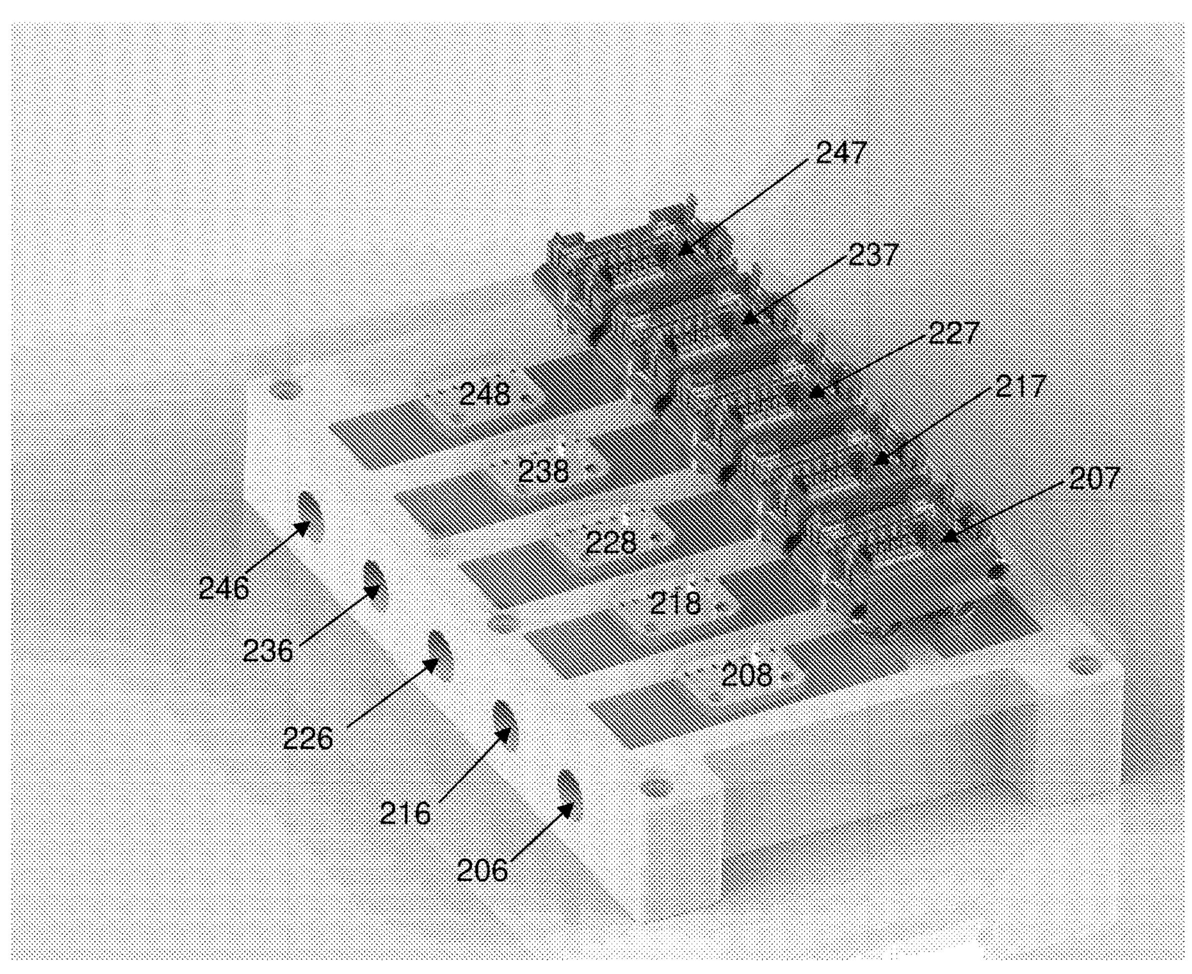
FIGS. 8 and 9 are 3D diagrams of the chambers for the dryness testing device of FIG. 7, with differential pressure sensors and humidity and temperature sensors.
Figure 9:
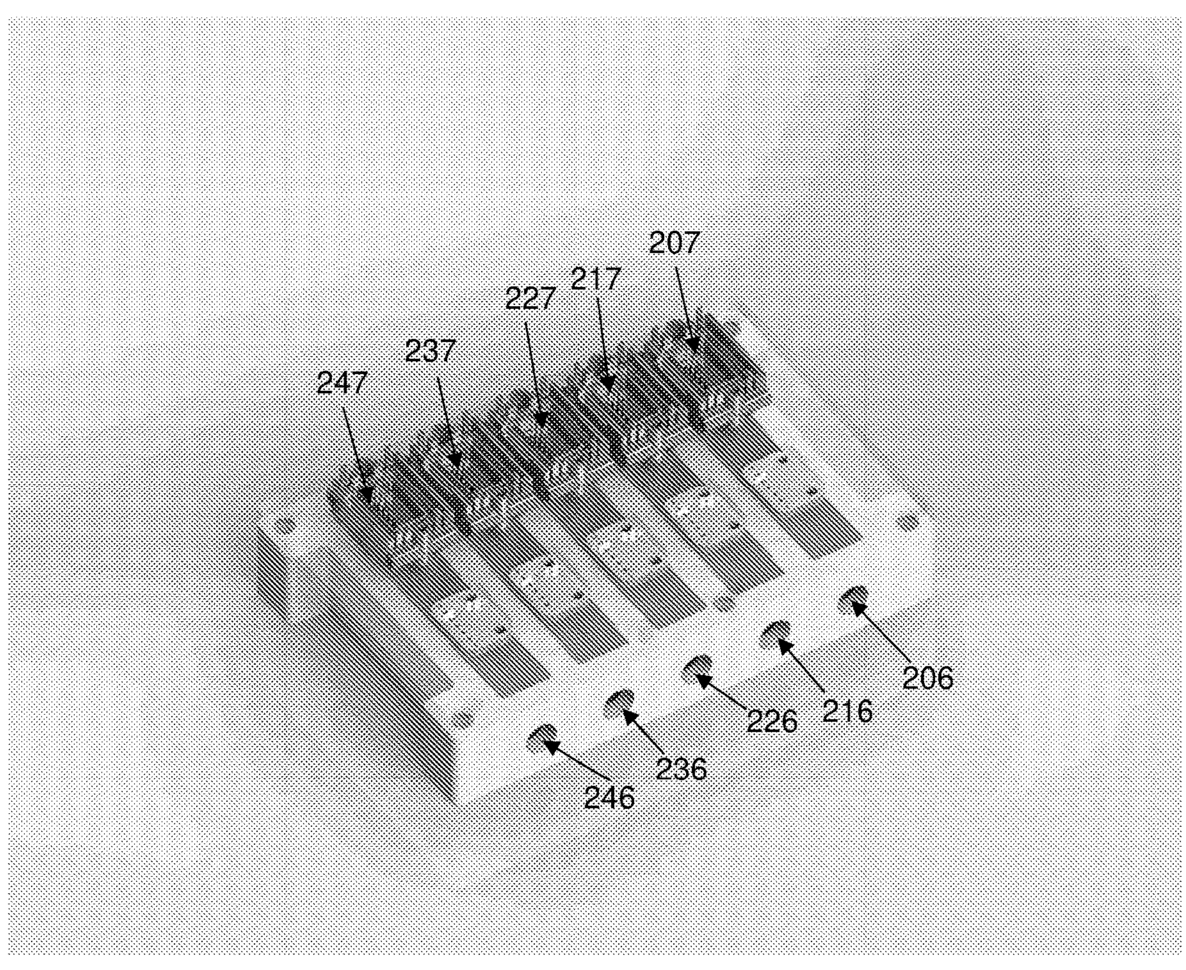

With reference to FIGS. 8 and 9, there is shown the 3D models of the chambers for the dryness testing device of FIG. 7, with five differential pressure sensors (207, 217, 227, 237, and 247) that are in connection with the first compartments and the second compartments. Each of the chambers also has an individual humidity and temperature sensor (208, 218, 228, 238, and 248).

Advantages

The preferred embodiment of the present invention provides an advantage that the dryness level of the interior of the reusable endoscope can be quantitatively tested and determined. The preferred embodiment provides a system and method of determining whether the endoscope tested has been successfully reprocessed. The preferred embodiment can also help to lower the risk of infection to a patient due to improper or unsuccessful reprocessing of the endoscope prior use.

In addition, the preferred embodiment can provide detailed and repeatable data sets for guidelines and recommendation for the drying time and method for each individual endoscope. The preferred embodiment can also provide validation on the drying function of the storage cabinet for the endoscope. Further, the preferred embodiment can provide validation whether or not there is continuous air flow in the internal channel for each individual endoscope during storage.

VARIATIONS

It will of course be realised that while the foregoing has been given by way of illustrative example of this invention, all such and other modifications and variations thereto as would be apparent to persons skilled in the art are deemed to fall within the broad scope and ambit of this invention as is herein set forth.

Throughout the description and claims of this specification the word "comprise" and variations of that word such as "comprises" and "comprising", are not intended to exclude other additives, components, integers or steps.

The invention claimed is:

1. A dryness testing device configured for determining the dryness of a medical instrument, said medical instrument comprising an endoscope including:

a proximal umbilical end comprising a plurality of instrument connections;

a distal end; and a plurality of channels to be tested, each of the plurality of channels comprising a proximal channel end connected to a respective one of the plurality of instrument connections and extending to the distal end of the endoscope to a distal channel end;

the dryness testing device comprising:

a cabinet comprising an internal space;

a cabinet manifold;

one or more chambers located within the internal cabinet space, each chamber configured for testing air flow from a respective channel of the medical instrument, wherein each of the one or more chambers comprises:

a first compartment and a second compartment separated by an internal dividing wall, the dividing wall comprising a substantially centred opening to allow air to pass through the first compartment to the second compartment;

a differential pressure sensor configured to determine rate of air flow between the first compartment and the second compartment;

a humidity and temperature sensor configured to measure the humidity and temperature of air in the second compartment;

an air inlet configured to connect air flow from a respective one of the plurality of instrument connections associated with a respective channel to be tested to a respective first compartment; and an air outlet configured to connect airflow from the second compartment to the cabinet manifold;

an extraction pump configured to cause air to be drawn from the cabinet, through the plurality of channels of the medical instrument when connected to a respective inlet port of a respective chamber; and into the cabinet manifold via the one or more chambers;

wherein:

the extraction pump causes air to be drawn into the distal end of each of the channels of the medical instrument into a respective one of the one or more chambers connected to a respective proximal umbilical end instrument connection for air measurements in the first and second compartments of the respective chamber; wherein the air measurements provide an indication of the dryness of the medical instrument; and the dryness testing device is configured for measuring the dryness of each of the plurality of channels of the medical instrument independently.

2. The dryness testing device as claimed in claim 1, wherein the indication of the dryness of the medical instrument is determined from the processed sensor measurements to provide quantitative values and or qualitative comparisons with external air.

3. The dryness testing device as claimed in claim 1, wherein the one or more chambers includes an inlet that is configured to include a releasable coupling for connecting to the medical instrument and an outlet that is configured to include a releasable coupling for connecting to an extraction means.

4. The dryness testing device as claimed in claim 3, wherein the inlet includes a filter for filtering particles in the air flow from the medical instrument.

5. The dryness testing device as claimed in claim 3, wherein the inlet includes a filter for breaking up droplets of liquid in the air flow from the medical instrument to promote evaporation of the droplets of liquid.

6. The dryness testing device as claimed in claim 1, wherein the differential pressure sensor associated with each of the one or more chambers that measures the pressure of the air in the first compartment of a respective chamber and the pressure of the air in the second compartment of the respective chamber, wherein the pressure difference from the two pressure readings is recorded and is used to calculate the air flow rate between the two compartments of the respective chamber.

7. The dryness testing device as claimed in claim 1, wherein each of the sensors associated with each of the one or more chambers sends data to a processor that collects and processes the data from the one or more sensors.

8. The dryness testing device as claimed in claim 1, wherein the dryness testing device includes an external air measurement chamber configured to measure air external to the medical instrument, the additional chamber comprising:

a first external air compartment and a second external air compartment separated by an internal dividing wall, the dividing wall comprising a substantially centred opening to allow air to pass through the first external air compartment to the second external air compartment;

a differential pressure sensor configured to determine rate of air flow of the external air between the first external air compartment and the second external air compartment;

a humidity and temperature sensor configured to measure the humidity and temperature of the external air in the second external air compartment;

an air inlet configured to connect air flow from the internal space of the cabinet to the first external air compartment; and an air outlet configured to connect airflow from the second external air compartment to the cabinet manifold;

wherein the external air measurement chamber is configured to measure the external air and to send external air sensor data to the processor wherein the processor is configured to: compare the quality of the external air with a quality of the air being drawn through the plurality of channels of the medical instrument, wherein, when the quality of the air being drawn through the medical instrument is substantially the same as a quality of the air that is external to the medical instrument, the medical instrument is considered to be dried.

9. A dryness testing device as claimed in claim 8 wherein the external air comprises air from the internal space of the cabinet.

10. A dryness testing system for a medical instrument, the system comprising:

one or more dryness testing devices of claim 1, wherein each dryness testing device includes:

one or more chambers configured to be connectable to the medical instrument and receive air flow from the medical instrument, each of the one or more chambers has an internal dividing wall that forms a first compartment and a second compartment, said internal dividing wall has a substantially centred opening to allow air to pass through the first compartment to the second compartment; and one or more sensors configured to assist in determining one or more flow rates, humidity and/or temperature of air being drawn through the medical instrument and drawn through the first compartment and the second compartment of each of the one or more chambers; wherein the measurements from the one or more sensors provides an indication of the dryness of the medical instrument; and one or more extraction pumps or extraction fans.

11. The dryness testing system as claimed in claim 10, further including one or more HEPA filters connected to an outlet of the dryness testing device.

12. The dryness testing system as claimed in claim 10, comprising:

a processor that receives data generated from the one or more sensors, wherein the processor includes a multiplexer and an interface board data processing unit, wherein the processor is configured to determine an absolute humidity value for each chamber, and wherein the absolute humidity value is determined from data collected from the one or more sensors including air flow rate, humidity and temperature.

13. The dryness testing system as claimed in claim 10, comprising:

a processor configured to compare an air flow rate associated with the medical instrument and a predetermined range of air flow rates;

wherein, when the processor determines that the air flow rate associated with the medical instrument is above the predetermined range of air flow rates, the processor sends a signal to an alarm system to indicate that the medical instrument is not connected, partially connected or incorrectly connected to the dryness testing device, and wherein when the processor determines that the air flow rate associated with the medical instrument is below the predetermined range of air flow rates, the processor sends a signal to the alarm system to indicate that there is a blockage within the internal channel of the medical instrument, within the connection between the medical instrument and the dryness testing device or within the dryness testing device.

14. The dryness testing system as claimed in claim 13, wherein the predetermined range of air flow rates is in a range of substantially two to three liters per minute.

15. The dryness testing system as claimed in claim 10, further includes an alarm system that receives a signal from a processor, wherein the alarm system is configured to notify an operator whether one or more ports of the medical instrument is successfully connected to the one or more chambers of the dryness testing device, and whether there is no blockage within any internal channel of the medical instrument, within the connection between the medical instrument and the dryness testing device, and within the dryness testing device.

16. The dryness testing system as claimed in claim 10, wherein the system is configured to be used with a drying and storing cabinet for the medical instrument, wherein the system is configured as an in-cabinet dryness testing system or as an out-of-cabinet dryness testing system.

17. The dryness testing system as claimed in claim 16, wherein the drying and storing cabinet is a blow-drying type drying and storing cabinet where air is pumped through the medical instrument, wherein the system further includes a switch that allows air to bypass the dryness testing device to pump through the internal channel of the medical instrument.

18. A dryness testing device as claimed in claim 1 wherein the dryness testing device is configured for measuring the dryness of each of the plurality of channels of the medical instrument simultaneously.

* * * * *